(12) United States Patent
     Kim

(10) Patent No.: US 11,141,200 B2
(45) Date of Patent: Oct. 12, 2021

(54) SPINAL FIXATION DEVICE

(71) Applicant: KYUNGPOOK NATIONAL UNIVERSITY INDUSTRY-ACADEMIC COOPERATION FOUNDATION, Daegu (KR)

(72) Inventor: Kyoung Tae Kim, Daegu (KR)

(73) Assignees: KYUNGPOOK NATIONAL UNIVERSITY, Daegu (KR); INDUSTRY-ACADEMIC COOPERATION FOUNDATION, Daegu (KR)

( * ) Notice: Subject to any disclaimer, the term of this patent is extended or adjusted under 35 U.S.C. 154(b) by 29 days.

(21) Appl. No.: 16/541,537

(22) Filed: Aug. 15, 2019

(65) Prior Publication Data
US 2020/0375630 A1    Dec. 3, 2020

(30) Foreign Application Priority Data
Jun. 3, 2019 (KR) .................. 10-2019-0065581

(51) Int. Cl.
*A61B 17/70* (2006.01)
*A61F 2/44* (2006.01)
*A61B 17/80* (2006.01)

(52) U.S. Cl.
CPC ........ *A61B 17/7037* (2013.01); *A61B 17/707* (2013.01); *A61B 17/7044* (2013.01); *A61B 17/80* (2013.01); *A61F 2/447* (2013.01); *A61B 17/7055* (2013.01); *A61B 17/7059* (2013.01); *A61B 17/7074* (2013.01); *A61F 2/4455* (2013.01)

(58) Field of Classification Search
None
See application file for complete search history.

(56) References Cited

U.S. PATENT DOCUMENTS

| 6,235,059 | B1 | 5/2001 | Benezech et al. |
| 10,342,675 | B2* | 7/2019 | Alheidt ................ A61F 2/4611 |
| 2008/0161925 | A1 | 7/2008 | Brittan et al. |
| 2008/0195158 | A1* | 8/2008 | De Villiers ........ A61B 17/7059 |
| | | | 606/280 |
| 2008/0294262 | A1 | 11/2008 | Levieux |
| 2008/0312742 | A1* | 12/2008 | Abernathie ............ A61F 2/447 |
| | | | 623/17.16 |
| 2010/0070037 | A1* | 3/2010 | Parry ...................... A61F 2/44 |
| | | | 623/17.16 |
| 2010/0249937 | A1 | 9/2010 | Blain et al. |

(Continued)

FOREIGN PATENT DOCUMENTS

| KR | 10-1041387 B1 | 6/2011 |
| KR | 10-1297982 B1 | 8/2013 |

(Continued)

*Primary Examiner* — Pedro Philogene
(74) *Attorney, Agent, or Firm* — Novick, Kim & Lee, PLLC; Sang Ho Lee; Hyun Woo Shin

(57) ABSTRACT

Provided is a spinal fixation device, which includes a cage which is placed between adjacent vertebrae to form a gap between the vertebrae, a middle plate which is detachably coupled to the cage, and deployment plates which are hinge-pivotably coupled to the middle plate at one side end, thereby stably fixing the cage in a correct position between the vertebrae.

18 Claims, 14 Drawing Sheets

(56) References Cited

U.S. PATENT DOCUMENTS

| | | |
|---|---|---|
| 2010/0274358 A1 | 10/2010 | Mueller et al. |
| 2011/0015745 A1 | 1/2011 | Bucci |
| 2012/0065688 A1 | 3/2012 | Nehls |
| 2014/0200670 A1* | 7/2014 | Chin .................. A61B 17/1757 623/17.16 |
| 2017/0189077 A1 | 7/2017 | Blain |
| 2018/0303629 A1* | 10/2018 | Lauf .................. A61B 17/7059 |

FOREIGN PATENT DOCUMENTS

| | | |
|---|---|---|
| KR | 10-2015-0084203 A | 7/2015 |
| KR | 10-1830547 B1 | 4/2018 |

\* cited by examiner

SPINAL FIXATION DEVICE

CROSS-REFERENCE TO RELATED APPLICATIONS

This application claims priority under 35 U.S.C. § 119 to Korean Patent Application No. 10-2019-0065581, filed on Jun. 3, 2019, in the Korean Intellectual Property Office, the disclosure of which is incorporated herein by reference in its entirety.

TECHNICAL FIELD

The present disclosure relates to a spinal fixation device, particularly, a spinal fixation device that is inserted and placed between adjacent vertebrae in spine or cervical spine surgeries.

BACKGROUND

In general, there are various spinal diseases including structural degenerative, congenital or traumatic displacement of the spine, such as spinal stenosis that occurs as the spinal canal narrows, or spondylolisthesis or retrolisthesis which is a misalignment of the vertebrae, and has severe symptoms which require surgical treatments.

One of the surgeries for spinal diseases is spinal fixation surgery in which a cage is inserted between the vertebrae. For example, conventionally, the surgery was performed by incising the portion of skin and muscle of a patient lying face down to expose the spine, removing an intervertebral disk, inserting a cage between the spinal nerves and branch nerves, and covering with a plate to fix the cage and vertebrae.

However, the surgical duration is prolonged in the process of placing the plate after inserting the cage, and the plate may be accidentally fixed obliquely or askew, or the plate may be fixed in such a way that one side is much longer than the other.

Particularly, because the surface of the vertebra is not smooth, the cage may be inserted and fixed in a direction that deviates from an intended direction at the time of bolting for fixation, resulting in inaccurate procedure.

Accordingly, technology for avoiding inaccurate procedures has been required.

SUMMARY

The present disclosure is designed to solve the conventional problem such as those described above, and therefore the present disclosure is directed to providing a spinal fixation device for fixing a cage accurately and stably after placing the cage between adjacent vertebrae.

To achieve the above-described object, a spinal fixation device according to a first embodiment of the present disclosure includes a cage which is placed between adjacent vertebrae to form a gap between the vertebrae, a middle plate which is detachably coupled to the cage, and deployment plates which are hinge-pivotably coupled to the middle plate at one side end.

Here, the coupling between the middle plate and the deployment plates may be hinge coupling.

Here, the coupling between the middle plate and the cage may be selectively detachable slide coupling.

Here, when the cage is inserted between the adjacent vertebrae to a predetermined level, the middle plate may be trapped in the vertebrae to prevent further insertion.

Here, a closer may be provided on a posterior side of the middle plate or the cage to prevent the deployment plates deployed by rotation to an arbitrary angle around the hinge coupling from being folded.

Here, a deployment limiting means may be provided in the deployment plates or the cage to limit the deployment of the deployment plates by rotation more than a predetermined angle around the hinge coupling.

Here, the spinal fixation device may further include a fixing means to fix the deployment plates to one of the adjacent vertebrae.

Further, the fixing means may be a fixing bolt, and the deployment plates may have a screw hole into which the fixing bolt is inserted for bolting with the vertebra.

Further, the deployment plates may have a bolt cover which covers at least part of the screw hole to prevent a head of the fixing bolt bolted to the vertebrae from protruding out of the screw hole.

Here, an artificial bone space for accommodating an artificial bone may be provided inside of the cage.

Here, the cage may have an artificial bone hole in communication with the artificial bone space.

To achieve the above-described object, a spinal fixation device according to a second embodiment of the present disclosure includes a cage which is placed between adjacent vertebrae to form a gap between the vertebrae, and deployment plates which are hinge-pivotably coupled to the cage at one side end.

Here, the coupling between the deployment plates and the cage may be hinge coupling.

Here, a step may be provided on a posterior side of the cage to cause the cage to be trapped in the vertebrae when the cage is inserted between the adjacent vertebrae to a predetermined level.

Here, a closer may be provided in the cage to prevent the deployment plates deployed by rotation to an arbitrary angle around the hinge coupling from being folded.

Here, a deployment limiting means may be provided on a posterior side of the deployment plates or the cage to limit the deployment of the deployment plates by rotation more than a predetermined angle around the hinge coupling.

Here, the spinal fixation device may further include a fixing means to fix the deployment plates to the adjacent vertebrae.

Further, the fixing means may be a fixing bolt, and the deployment plates may have a screw hole into which the fixing bolt is inserted for bolting with the vertebra.

Further, the deployment plates may have a bolt cover which covers at least part of the screw hole to prevent a head of the fixing bolt bolted to the vertebrae from protruding out of the screw hole.

Here, an artificial bone space for accommodating an artificial bone may be provided inside of the cage.

Here, the cage may have an artificial bone hole in communication with the artificial bone space.

The spinal fixation device according to the present disclosure can fix the cage inserted and placed between the vertebrae accurately and stably, ensuring accuracy of cage insertion surgical procedure stably.

DETAILED DESCRIPTION OF EMBODIMENTS

Hereinafter, the preferred embodiments will be described with reference to the accompanying drawings to provide a further understanding of the present disclosure.

First, to help the description and understanding of the embodiments of the present disclosure, in the specification, the anterior side of the cage refers to the front side that is earlier inserted between adjacent vertebrae. Accordingly, the posterior side is the rear side that is opposite to the anterior side.

Furthermore, in the side view which reference is made for description, the right side is the anterior side of the spinal fixation device and the cage, and the left side of the side view is the posterior side of the spinal fixation device and the cage.

Figure 1:
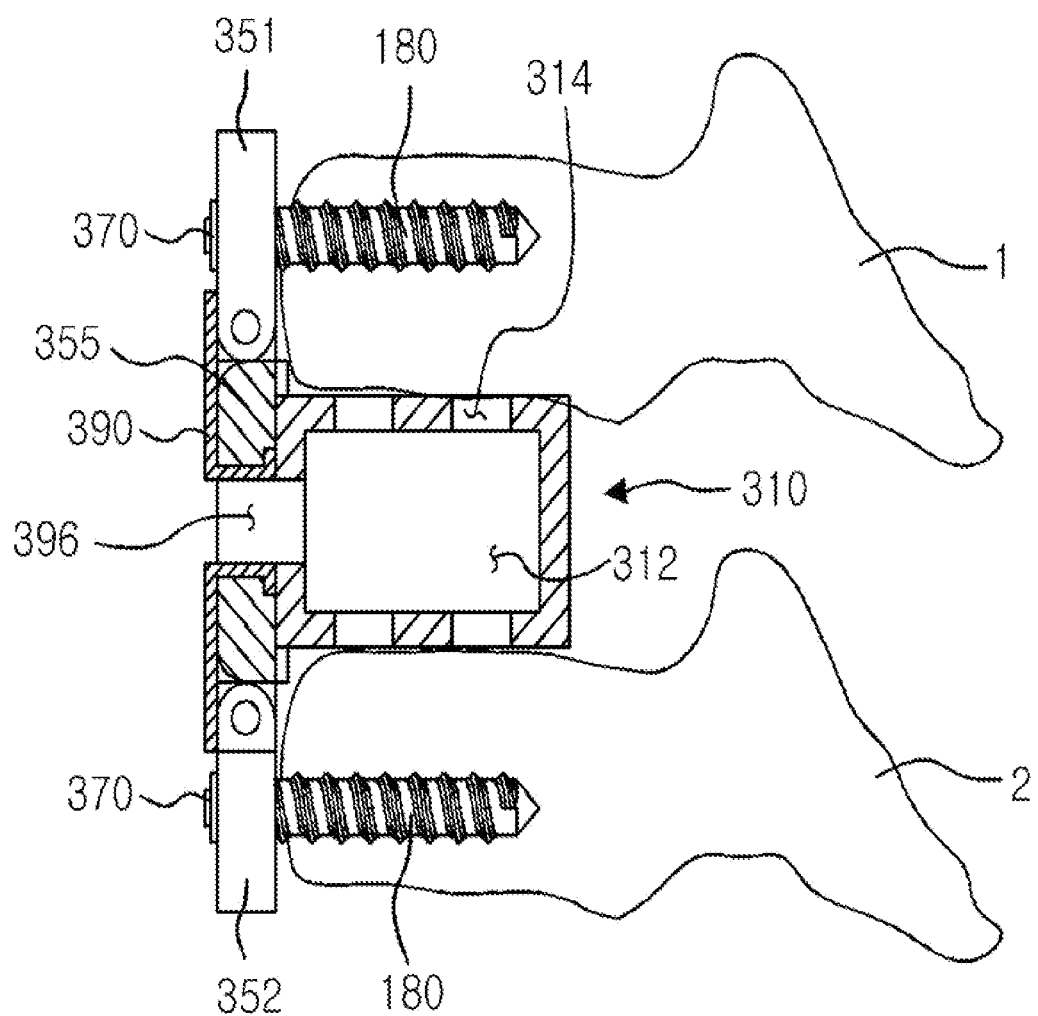
FIG. 1 is a schematic side cross-sectional view showing a spinal fixation device placed between adjacent vertebrae according to a first embodiment of the present disclosure.

FIG. 1 is a schematic side cross-sectional view showing a spinal fixation device placed between adjacent vertebrae according to a first embodiment of the present disclosure.

Referring to FIG. 1, the spinal fixation device according to the first embodiment of the present disclosure includes a cage 310, a middle plate 355 and deployment plates 351, 352.

The cage 310 has an arbitrary size, and is placed between the adjacent vertebrae 1, 2 to form a gap between the vertebrae 1, 2.

As can be seen from FIG. 1, the cage 310 has an arbitrary size to form the gap between the adjacent vertebrae 1, 2.

Additionally, an artificial bone space 312 for accommodating an artificial bone (not shown) is preferably provided inside of the cage 310. After the spinal fixation device 300 is placed between the vertebrae 1, 2, the artificial bone may be implanted into the artificial bone space 312 of the cage 310.

The material of the cage 310 is polymer resin with high strength, high rigidity, high temperature resistance and chemical resistance, and preferably made of biomaterials used in MRI and medical implants. For example, the cage 310 is preferably made of Poly Ether Ether Ketone (PEEK).

Additionally, the cage 310 preferably has an artificial bone hole 314 in communication with the artificial bone space 312. FIG. 1 exemplarily shows that the artificial bone hole 314 is formed on the upper side and the lower side of the cage 310.

The middle plate 355 is coupled to the posterior side of the cage 310.

Additionally, the deployment plates 351, 352 are coupled with the middle plate 355 and provided for fixation to the adjacent vertebrae 1, 2.

Here, the coupling between the cage 310 and the middle plate 355 will be described with further reference to FIG. 2.

Figure 2:
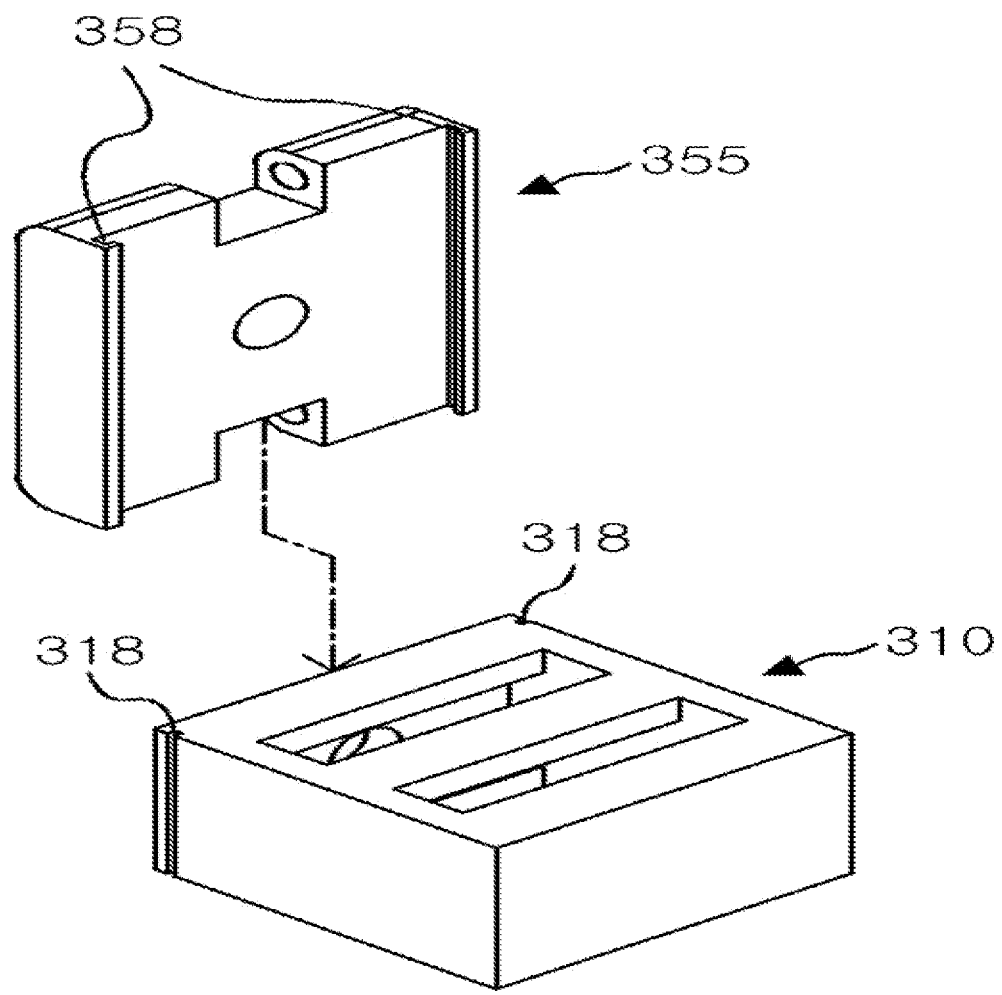
FIG. 2 is a schematic perspective view showing coupling between a middle plate and a cage in a spinal fixation device according to a first embodiment of the present disclosure.

FIG. 2 is a schematic diagram showing the middle plate 355 and the cage 310 in the spinal fixation device according to the first embodiment of the present disclosure.

As can be seen from FIGS. 1 and 2, the middle plate 355 is coupled to the posterior side of the cage 310. Preferably, the coupling between the middle plate 355 and the cage 310 is selectively detachable coupling.

The selectively detachable form between the middle plate 355 and the cage 310 may be slide coupling. FIG. 2 shows the form of selectively detachable coupling by slide coupling between the middle plate 355 and the cage 310.

A slide groove 358 is provided on the anterior side of the middle plate 355 for slide coupling with the cage 310. Additionally, the cage 310 has a slide groove 318 of a shape that can be coupled to match the slide groove 358 of the middle plate 355.

Accordingly, as can be seen from FIG. 2, the middle plate 355 may be slide coupled with the cage 310.

When the coupling between the middle plate 355 and the posterior side of the cage 310 is accomplished by slide coupling 358, 318 as described above, the cage 310 of an appropriate shape may be mounted in the middle plate 355 according to the user or procedural needs. Alternatively, it is possible to replace with a different shaped cage.

Accordingly, any one cage 310 having a suitable shape for the procedure may be selected from many cages having various shapes or sizes for one middle plate 355, and may be coupled with the middle plate 355 and used in the procedure.

When the coupling between the middle plate 355 and the posterior side of the cage 310 is a detachable coupling like the slide coupling 318, 358, it is preferable in that different cages having different sizes or shapes can be selectively replaced or changed as necessary.

Figure 4:
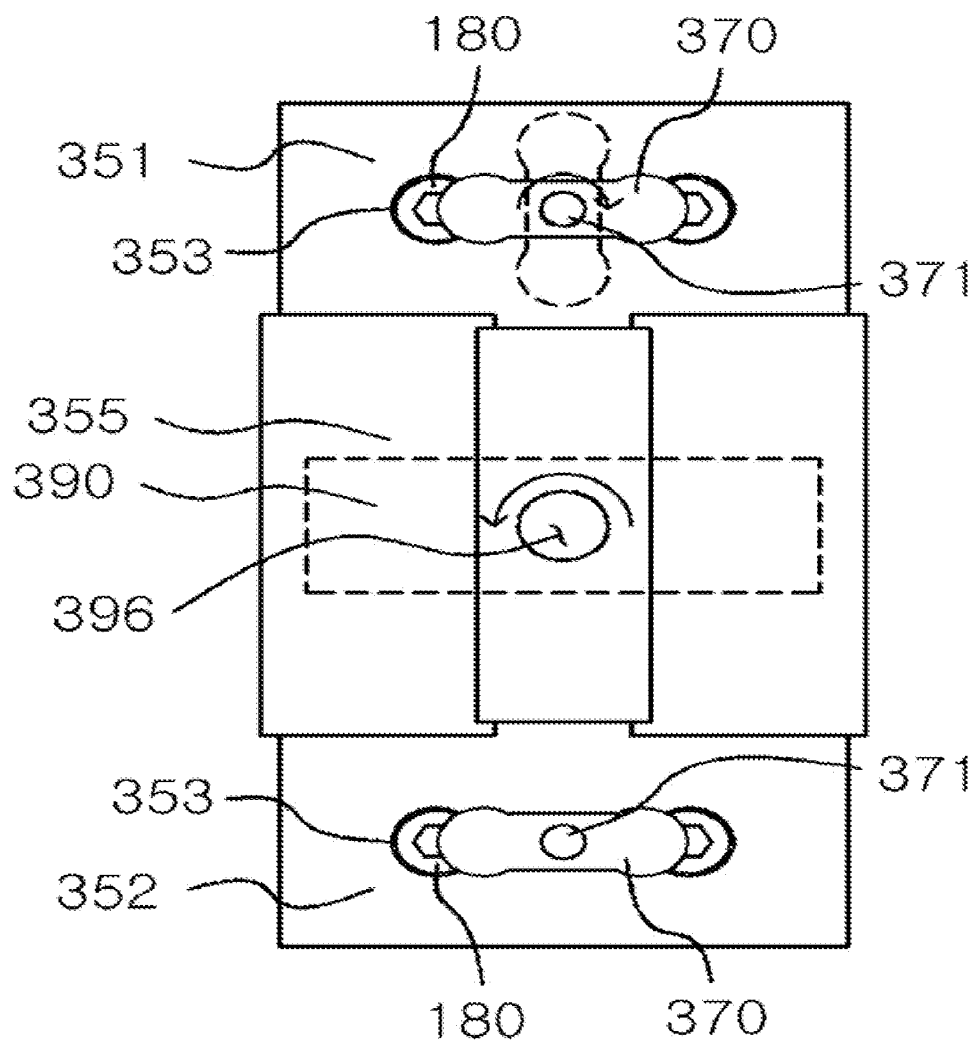
FIG. 4 is a schematic diagram showing the posterior side of a spinal fixation device according to a first embodiment of the present disclosure.

Additionally, as can be seen from FIG. 4, the height of the middle plate 355 is preferably greater than the height of the cage 310, so that the middle plate 355 is trapped in the vertebrae 1, 2 when the cage 310 is inserted between the adjacent vertebrae 1, 2 to a predetermined level.

When the height of the middle plate 355 is greater than the height of the cage 310, the middle plate 355 is trapped in the vertebrae 1, 2 when inserting the cage 310 between the two vertebrae 1, 2, and thus it is possible to prevent the cage 310 from being accidentally inserted too deeply.

Subsequently, the deployment plates 351, 352 will be described with reference to FIG. 1 and with further reference to FIG. 3.

Figure 3:
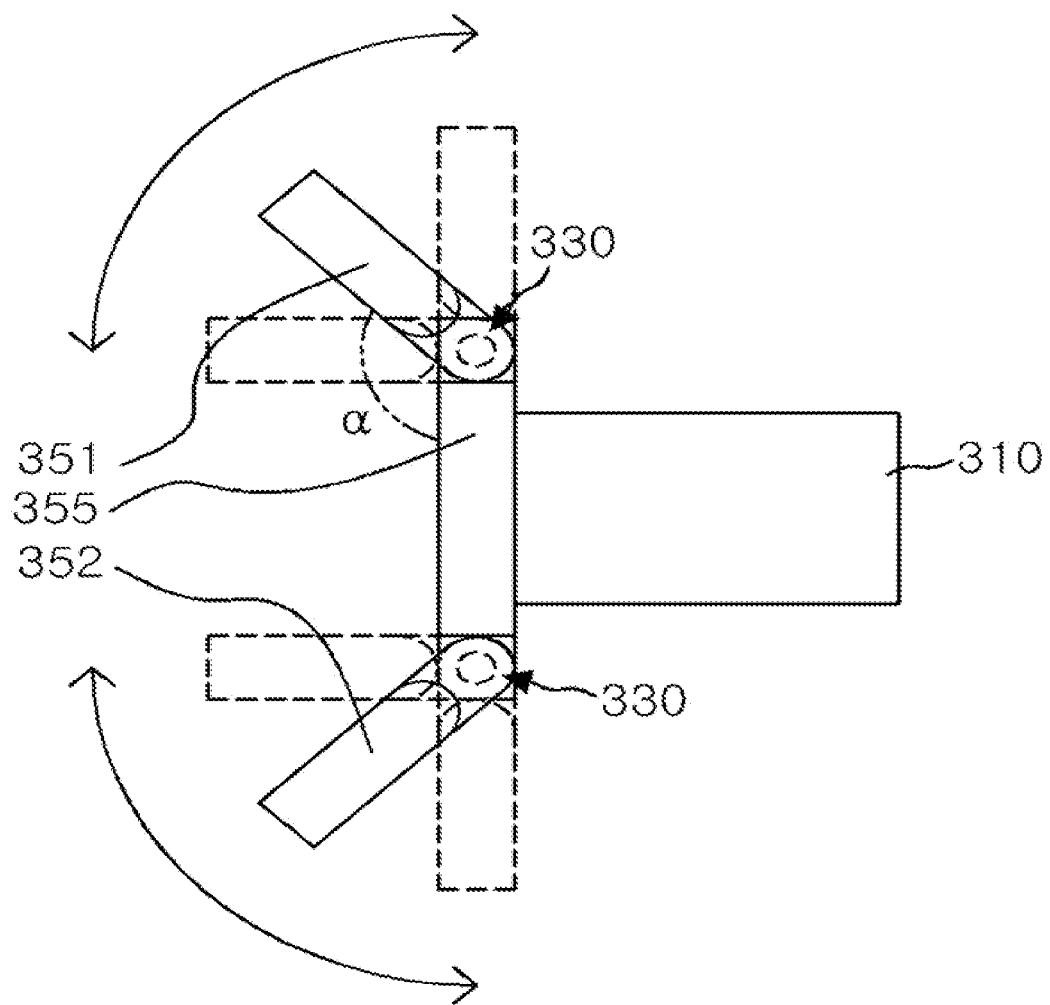
FIG. 3 is a schematic side view showing rotation of deployment plates coupled to a middle plate in a spinal fixation device according to a first embodiment of the present disclosure.

FIG. 3 is a schematic side view showing rotation of the deployment plates 351, 352 coupled to the middle plate 355 in the spinal fixation device according to the first embodiment of the present disclosure.

Referring to FIGS. 1 and 3, the deployment plates 351, 352 are, at one side end, hinge-pivotably coupled to the middle plate 355. Additionally, the deployment plates 351, 352 may rotate to an arbitrary angle α around the coupled parts between the middle plate 355 and the deployment plates 351, 352.

Preferably, the coupling between the middle plate 355 and the deployment plates 351, 352 is hinge coupling 330.

The deployment plates 351, 352 are hinge-coupled with the middle plate 355, and fixed to one of the adjacent vertebrae 1, 2.

In more detail, one side end of the upper deployment plate 351 is coupled to the upper end of the middle plate 355, or one side end of the lower deployment plate 352 is coupled to the lower end of the middle plate 355.

As described above, the deployment plates 351, 352 are hinge-coupled 330 to the middle plate 355, so the deployment plates 351, 352 may rotate to the arbitrary angle α around the center axis of the hinge coupling 330.

The coupling angle α between the deployment plates 351, 352 and the posterior side surface of the middle plate 355 is about 90° until the cage 310 is placed between the adjacent vertebrae 1, 2.

Here, as can be seen from the drawing, it can be said that the deployment plates 351, 352 are folded relative to the middle plate 355 with respect to the hinge coupling 330.

When the cage 310 is inserted between the adjacent vertebrae 1, 2, the deployment plates 351, 352 rotate around the hinge coupling 330 to fix the position of the cage 310 without change, as can be seen from FIG. 3.

Additionally, when the deployment plates 351, 352 are unfolded by rotation, the coupling angle α between the posterior side of the middle plate 355 and the deployment plates 351, 352 increases. Preferably, the coupling angle α increases to 180°.

As described above, it can be said that the deployment plates 351, 352 are unfolded relative to the middle plate 355, and the deployment plates 351, 352 are deployed.

In FIG. 3, when the deployment plates 351, 352 are deployed by unfolding with respect to the hinge coupling 330 with the middle plate 355 such as at the coupling angle α of 180°, one side surface of the deployment plate 351, 352 is near or in contact with the vertebrae 1, 2.

When the deployment plate 351, 352 near or in contact with the vertebrae 1, 2 is coupled to the vertebrae 1, 2 by a fixing means as described below, the middle plate 355 hinge-coupled 330 with the deployment plates 351, 352 fixed to the vertebrae 1, 2 supports the cage 310.

The deployment plates 351, 352 are preferably made of biocompatible materials. The use of the biocompatible materials may suppress the rejection reaction in the body. For example, the deployment plates 351, 352 are preferably made of materials with high biocompatibility and durability such as titanium.

Preferably, the spinal fixation device may further include a fixing means, and this will be described with reference to FIGS. 1 and 4.

FIG. 4 is a schematic diagram showing the posterior side of the spinal fixation device according to the first embodiment of the present disclosure.

Referring to FIGS. 1 and 4, in the spinal fixation device according to the first embodiment of the present disclosure, the fixing means fixes the deployment plates 351, 352 to the adjacent vertebrae 1, 2.

A preferable example of the fixing means is a fixing bolt 180. The deployment plates 351, 352 preferably have a screw hole 353 into which the fixing bolt 180 is inserted for bolting with the vertebrae 1, 2.

The fixing bolt 180 may be inserted through the screw hole 353 provided in the deployment plates 351, 352 and bolted to the vertebrae 1, 2, and the position of the cage 310 placed between the adjacent vertebrae 1, 2 may be fixed.

Additionally, each of the deployment plates 351, 352 preferably has a bolt cover 370 which covers at least part of the screw hole 353 to prevent the head of the fixing bolt 180 bolted to the vertebrae 1, 2 from protruding out of the screw hole 353.

As shown in FIGS. 1 and 4, the deployment plates 351, 352 have the bolt cover 370. The bolt cover 370 may be coupled with the deployment plates 351, 352 through a cover center axis 371, and the bolt cover 370 may rotate around the cover center axis 371.

When the fixing bolt 180 is bolted to the vertebrae 1, 2 through the screw hole 353, in order to prevent the head of the fixing bolt 180 from protruding out of the screw hole 353, the bolt cover 370 covers at least part of the screw hole 353 by rotation around the cover center axis 371. As at least part of the screw hole 353 is covered with the bolt cover 370, the release of the fixing bolt 180 is prevented.

Additionally, the middle plate 355 preferably includes a closer 390.

The closer 390 is provided in the middle plate 355 to maintain the unfolded state of the deployment plates 351, 352 deployed by rotation around the hinge coupling with the middle plate 355, while preventing the deployment plates 351, 352 from being folded again in the reverse direction.

As shown in FIG. 1, the closer 390 is rotatably coupled on the posterior side of the middle plate 355. As indicated as the dashed line in FIG. 4, the closer 390 is in a state of not disturbing the movement of the deployment plates 351, 352 until the deployment plates 351, 352 are unfolded to 180°.

Subsequently, when the deployment plates 351, 352 are deployed 180°, the closer 390 covers part of the deployment plates 351, 352 by rotation to maintain the deployed state of the deployment plates 351, 352 without being folded again. Here, the closer 390 is preferably rotatable around the coupled part with the middle plate 355.

When the closer 390 rotates, two ends of the closer 390 cover the hinge-coupled parts of the deployment plates 351, 352 on the posterior side of the cage 310, as can be seen from FIGS. 1 and 4.

Accordingly, because the two ends of the closer 390 prevent the deployment plates 351, 352 from being folded, the deployment plates 351, 352 can maintain the deployed state.

Additionally, a holding hole 396 is preferably provided at the center of rotation of the closer 390 for a cage holder (not shown) to hold.

Preferably, a screw thread is formed on the inner peripheral surface of the holding hole 396 for coupling with a holder rod (not shown) of the cage holder. When the holder rod is bolt-coupled to the holding hole 396, the spinal fixation device may be held by the cage holder.

For reference, a hole in communication with the holding hole 396 of the closer 390 is preferably provided on the posterior side of the cage 310. Preferably, the hole of the cage 310 in communication with the holding hole 396 of the closer 390 also has a screw thread for coupling with the holder rod.

Subsequently, a spinal fixation device according to a second embodiment of the present disclosure will be described.

Here, in the same way as the first embodiment described previously, to help the description and understanding, the anterior side of the cage refers to the front side that is earlier inserted between adjacent vertebrae. Accordingly, the posterior side refers to the rear side that is opposite to the anterior side.

Additionally, as in the description of the embodiment described previously, in the side view, the right side is the anterior side of the cage, and the left side is the posterior side of the cage.

Figure 5:
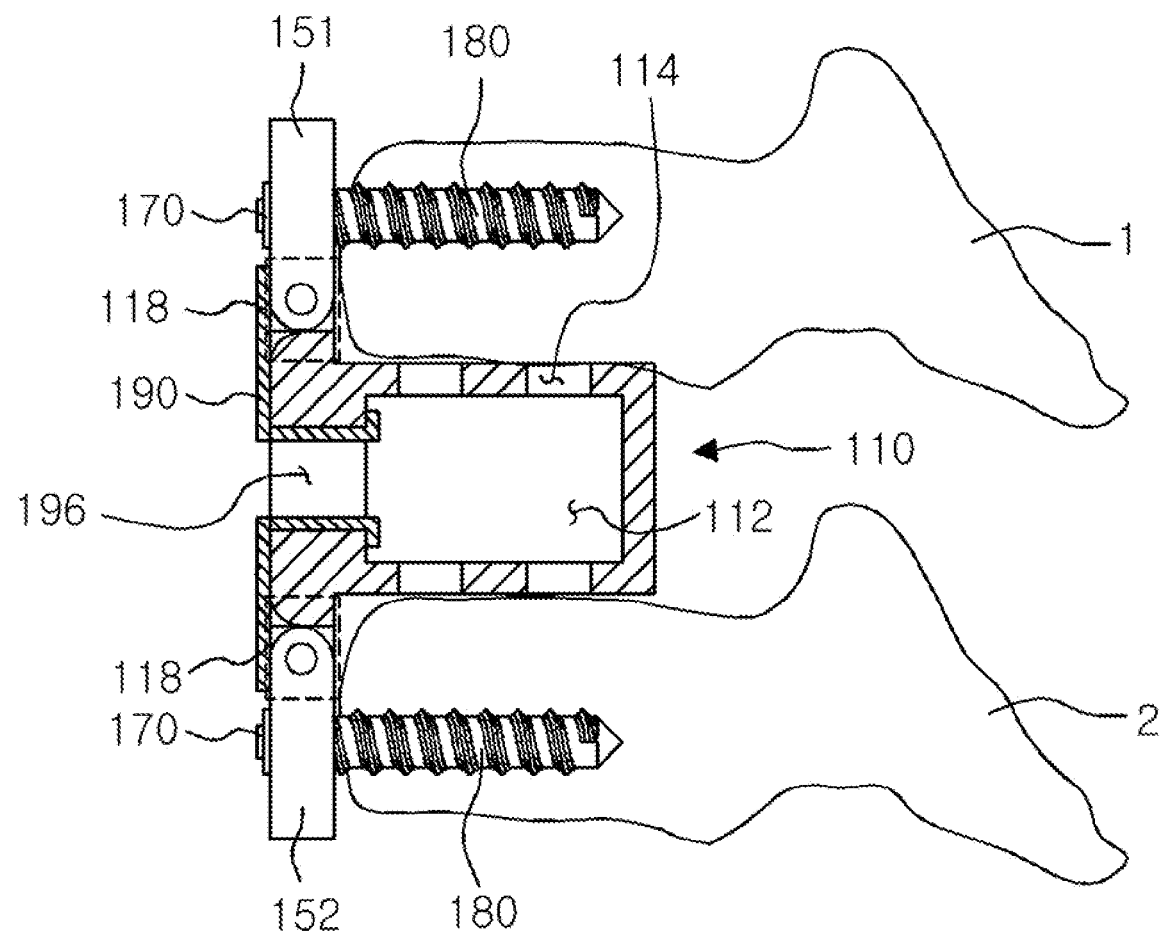
FIG. 5 is a schematic side cross-sectional view showing a spinal fixation device placed between adjacent vertebrae according to a second embodiment of the present disclosure.

FIG. 5 is a schematic side cross-sectional view showing the spinal fixation device placed between adjacent vertebrae according to the second embodiment of the present disclosure.

Describing with reference to FIG. 5, the spinal fixation device according to the second embodiment of the present disclosure includes a cage 110 and deployment plates 151, 152.

The cage 110 has an arbitrary size. The cage 110 is inserted and placed between the adjacent vertebrae 1, 2 to form a gap between the vertebrae 1, 2.

Additionally, an artificial bone space 112 for accommodating an artificial bone (not shown) is preferably provided inside of the cage 110. After the cage 110 is inserted and placed between the vertebrae 1, 2, the artificial bone or synthetic bone substitute (hereinafter referred to collectively as artificial bone) may be implanted into the artificial bone space 112 of the cage 110.

The material of the cage 110 is polymer resin with high strength, high rigidity, high temperature resistance and chemical resistance, and preferably made of biomaterials used in MRI and medical implants. For example, the cage 110 is preferably made of Poly Ether Ether Ketone (PEEK).

Additionally, the cage 110 preferably has an artificial bone hole 114 in communication with the artificial bone space 112. FIG. 5 exemplarily shows that the artificial bone hole 114 is formed on the upper side and the lower side of the cage 110.

It is preferable to prevent the cage 110 from being accidentally inserted too deeply when inserting the cage 110 between the two vertebrate 1, 2. Accordingly, a step 118 that causes the cage 110 to be trapped in the vertebrae 1, 2 when the cage 110 is inserted between the adjacent vertebrae 1, 2 to a predetermined level is preferably provided on the posterior side of the cage 110.

Additionally, the deployment plates 151, 152 are coupled to the posterior side of the cage 110. The deployment plates 151, 152 are provided to be fixed to the adjacent vertebrae 1, 2.

Additionally, preferably, the deployment plates 151, 152 may rotate to an arbitrary angle around the coupled parts 130 between the cage 110 and the deployment plates 151, 152.

Here, rotation of the deployment plates 151, 152 will be described with further reference to FIG. 6.

Figure 6:
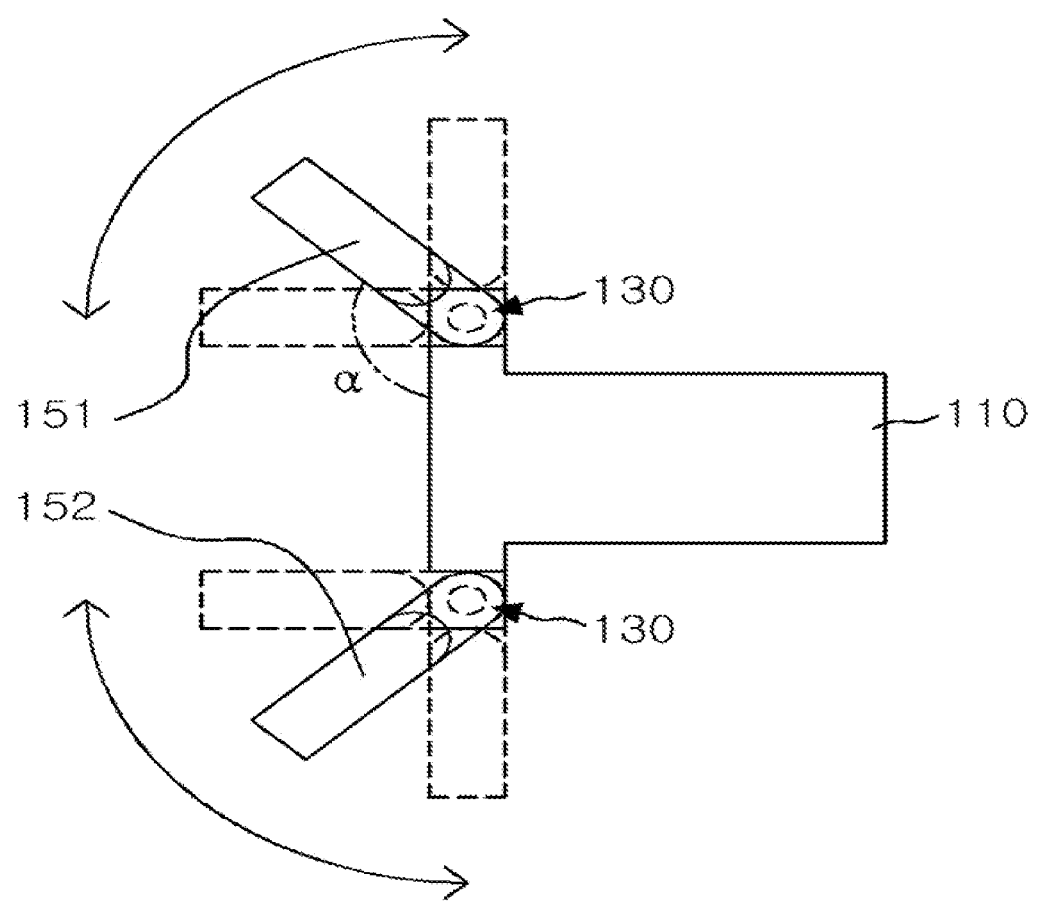
FIG. 6 is a schematic side view showing rotation of deployment plates coupled to a cage in a spinal fixation device according to a second embodiment of the present disclosure.

FIG. 6 is a schematic side view showing that the deployment plates 151, 152 are rotatably coupled to the posterior side of the cage 110 and rotate to an arbitrary angle α in the spinal fixation device according to the second embodiment of the present disclosure.

As can be seen from FIGS. 5 and 6, one side end of the deployment plates 151, 152 is coupled to part of the posterior side of the cage 110. Preferably, one side end of the deployment plates 151, 152 is hinge-pivotably coupled to the cage 110.

Accordingly, the deployment plates 151, 152 coupled to the posterior side of the cage 110 may rotate to the arbitrary angle α around the coupled parts 130.

Preferably, one side end of the deployment plates 151, 152 is hinge-coupled 130 to part of the posterior side of the cage 110 for the deployment plates 151, 152 to rotate.

As described above, the deployment plates 151, 152 may rotate to the arbitrary angle α around the center axis of the hinge coupling 130.

Here, the angle α between the deployment plates 151, 152 and the posterior side surface of the cage 110 around the center axis of the hinge coupling 130 is referred to as a coupling angle α between the deployment plate 151, 152 and the cage 110.

The coupling angle α between the deployment plates 151, 152 and the posterior side surface of the cage 110 is about 90° until the spinal fixation device 100 is placed between the adjacent vertebrae 1, 2, and it can be said that the deployment plates 151, 152 are folded relative to the cage 110 with respect to the hinge coupling 130.

Additionally, when the cage 110 is inserted and placed between the adjacent vertebrae 1, 2, to fix the position of the cage 110 without change, as can be seen from FIG. 6, the deployment plates 151, 152 may rotate around the hinge coupling 130.

Here, the coupling angle α between the posterior side of the cage 110 and the deployment plates 151, 152 increases. Preferably, the coupling angle α increases to 180°.

It can be said that the deployment plates 151, 152 are unfolded relative to the cage 110, and the deployment plates 151, 152 are deployed.

Additionally, the coupling angle α of 180° is as shown in FIG. 5.

When the deployment plates 151, 152 near or in contact with the vertebrae 1, 2 are fixed to the vertebrae 1, 2, because the cage 110 is coupled with the deployment plates 151, 152, as a result, the cage 110 is fixed between the two vertebrae 1, 2.

Preferably, a plurality of deployment plates 151, 152 is provided. As can be seen from the drawing, preferably, on the posterior side of the cage 110, one deployment plate 151 is coupled to the upper side and the other deployment plate 152 is coupled to the lower side.

The deployment plates 151, 152 are preferably made of biocompatible materials. The use of the biocompatible materials may suppress the rejection reaction in the body. For example, the deployment plates 151, 152 are preferably made of materials with high biocompatibility and durability such as titanium.

Here, a fixing means will be described with further reference to FIGS. 7A and 7B.

Figure 7A:
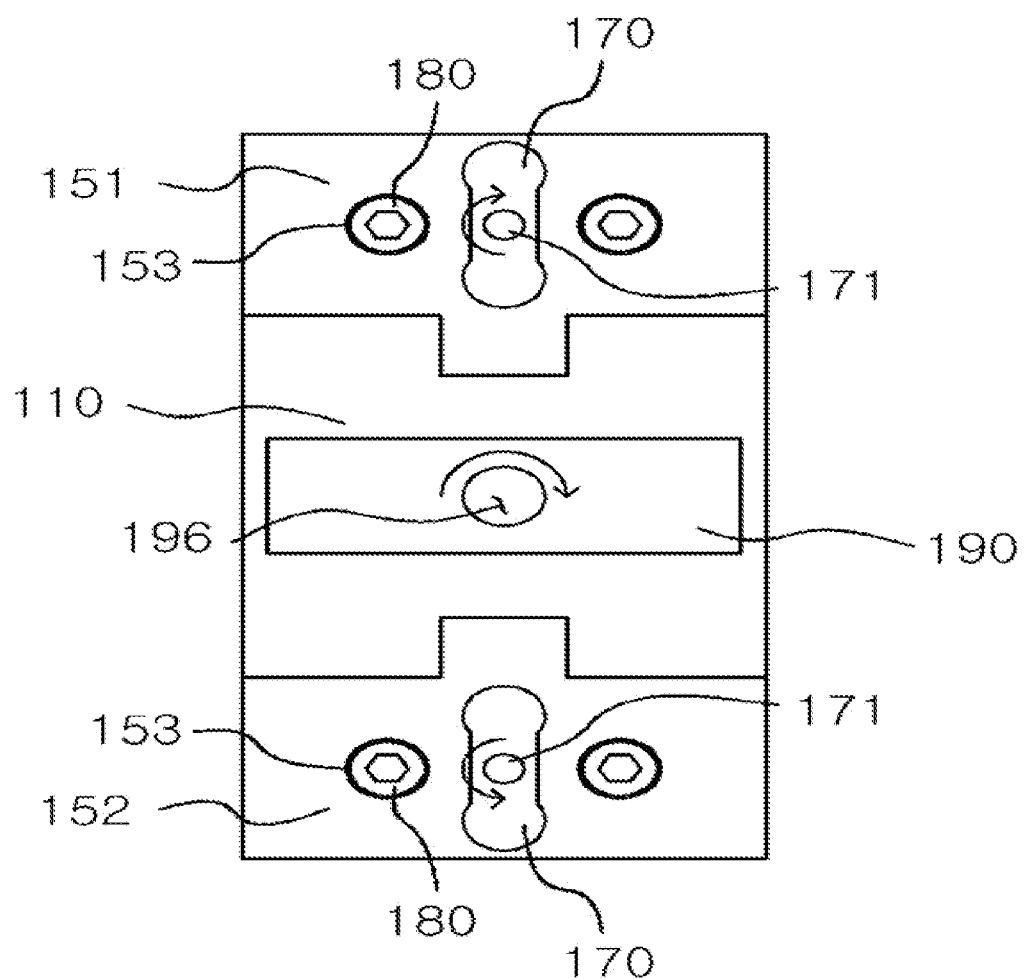
FIGS. 7A and 7B are schematic diagrams showing the posterior side of a spinal fixation device according to a second embodiment of the present disclosure.
Figure 7B:
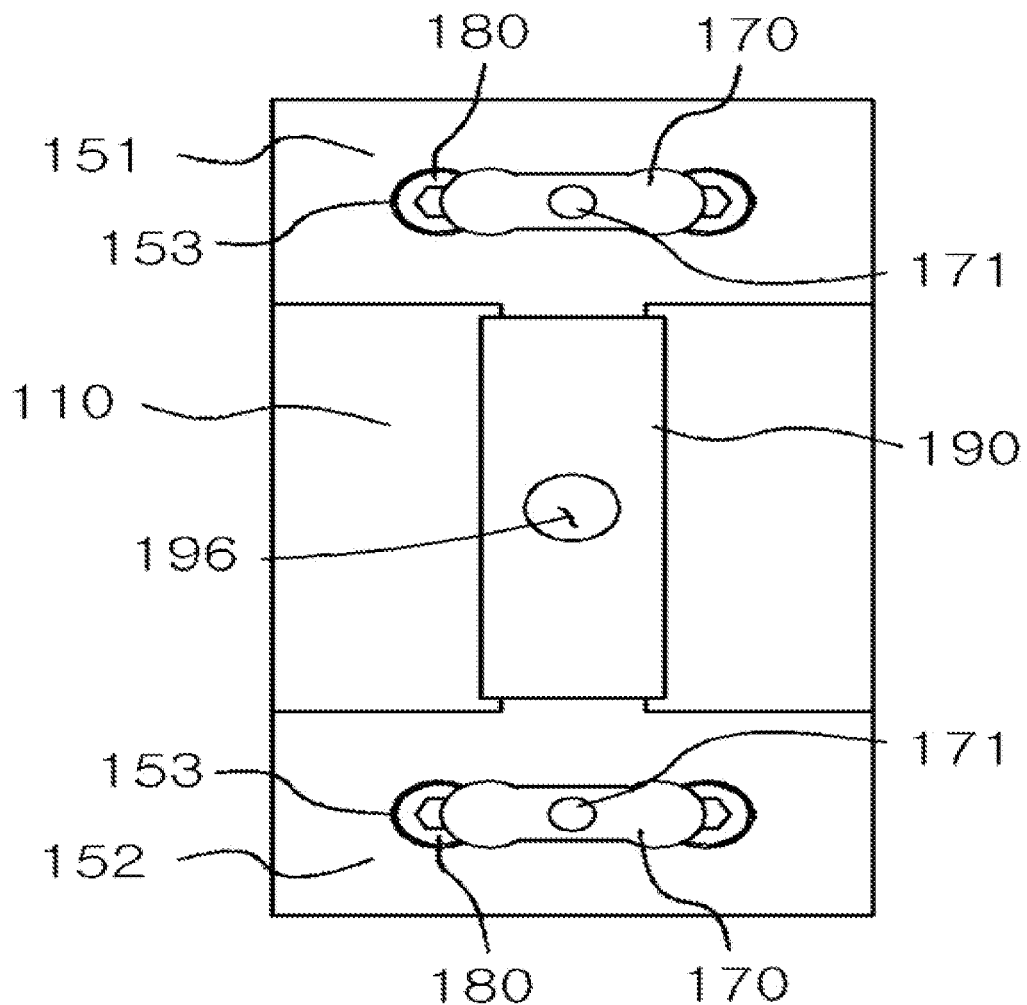

FIGS. 7A and 7B are schematic diagrams showing the posterior side of the spinal fixation device according to the second embodiment of the present disclosure.

Referring to FIGS. 5, 7A and 7B, the fixing means fixes the deployment plates 151, 152 to the adjacent vertebrae 1, 2.

A preferable example of the fixing means is a fixing bolt 180, and in this case, the deployment plates 151, 152 preferably has a screw hole 153 into which the fixing bolt 180 is inserted for bolting with the vertebrae 1, 2.

The fixing bolt 180 may be inserted through the screw hole 153 provided in the deployment plates 151, 152 and bolted to the vertebrae 1, 2, and the position of the cage 110 placed between the adjacent vertebrae 1, 2 may be fixed.

Additionally, each of the deployment plates 151, 152 preferably has a bolt cover 170 which covers at least part of the screw hole 153 to prevent the head of the fixing bolt 180 bolted to the vertebrae 1, 2 from protruding out of the screw hole 153.

As can be seen from FIG. 7A, the deployment plates 151, 152 have the bolt cover 170. The bolt cover 170 may be coupled with the deployment plates 151, 152 through a cover center axis 171, and the bolt cover 170 may rotate around the cover center axis 171.

As can be seen from FIG. 7B, when the fixing bolt 180 is bolted to the vertebrae 1, 2 through the screw hole 153, in order to prevent the head of the fixing bolt 180 from protruding out of the screw hole 153, the bolt cover 170 covers at least part of the screw hole 153 by rotation around the cover center axis 171. As at least part of the screw hole 153 is covered with the bolt cover 170, the release of the fixing bolt 180 is prevented.

Additionally, as can be seen from FIGS. 5, 7A and 7B, a closer 190 is preferably provided to maintain the unfolded state of the deployment plates 151, 152 deployed such that the arbitrary angle α is 180° with respect to the hinge coupling 130 without being folded again in the reverse direction.

That is, the closer 190 is provided in the cage 110 to prevent the deployment plates 151, 152 deployed by rotation to the arbitrary angle α around the hinge coupling 130 from being folded.

As shown in FIG. 5, the closer 190 is rotatably coupled to the posterior side of the cage 110. As shown in FIG. 7A, the closer 190 is in a state of not disturbing the movement of the deployment plates 151, 152 until the deployment plates 151, 152 are unfolded to 180°.

Subsequently, when the deployment plates 151, 152 are deployed 180°, the closer 190 may rotate to maintain the deployed state of the deployment plates 151, 152 without being folded again. Here, the closer 190 is preferably rotatable around the coupled part with the cage 110.

When the closer 190 rotates, two ends of the closer 190 cover the hinge-coupled parts of the deployment plates 151, 152 on the posterior side of the cage 110 as shown in FIG. 7B.

Accordingly, because the two ends of the closer 190 prevent the deployment plates 151, 152 from being folded, the deployment plates 151, 152 can maintain the deployed state.

Additionally, a holding hole 196 is preferably provided at the center of rotation of the closer 190 for a cage holder (not shown) to hold.

Preferably, a screw thread is formed on the inner peripheral surface of the holding hole 196 for coupling with a holder rod (not shown) of the cage holder. When the holder rod is bolt-coupled to the holding hole 196, the spinal fixation device may be held by the cage holder.

Preferably, the spinal fixation device of the embodiments as described hereinabove further includes a deployment limiting means as below.

Figure 8:
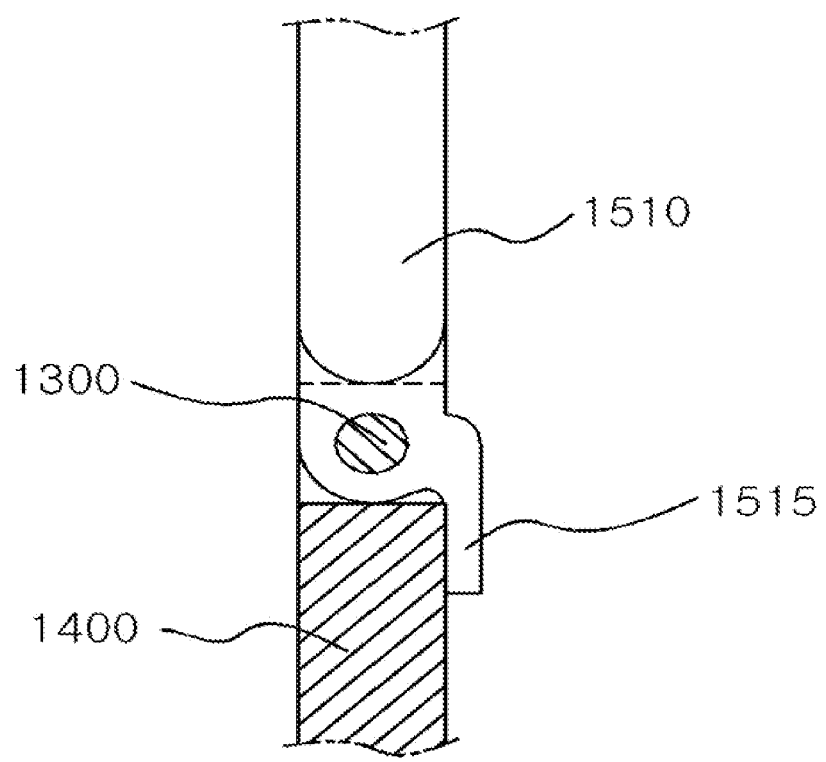
FIGS. 8 to 11 are schematic partial enlarged views showing a deployment limiting means that may be further included in a spinal fixation device according to a first embodiment of the present disclosure.

FIG. 8 is a schematic partial enlarged view showing an exemplary type of the deployment limiting means that may be further included in the spinal fixation device according to the embodiments of the present disclosure.

Referring to FIG. 8, the deployment limiting means limits the rotation of the deployment plate 1510 exceeding 180° when the deployment plate 1510 rotates around the hinge coupling 1300.

A preferable example of the deployment limiting means is a deployment limiter 1515.

In the case of the spinal fixation device of the first embodiment described previously, the deployment limiter 1515 is preferably provided on the posterior side of the deployment plate 1510 to limit the deployment of the deployment plate 1510 more than a predetermined angle with respect to the hinge coupling 1300.

Here, the reference numeral 1400 indicates the middle plate 355 (see FIG. 4) of the first embodiment. The deployment limiter 1515 limits the deployment of the deployment plate 1510 more than a predetermined angle when contacting a part of the posterior side of the middle plate 1400.

Additionally, a maximum rotatable angle is preferably 180°. If the deployment plate 1510 rotates more than 180°, the cage may be separated from the vertebrae.

Accordingly, the deployment limiter 1515 is provided to prevent the separation of the cage caused by rotation of the deployment plate 1510 more than 180°.

Figure 9:
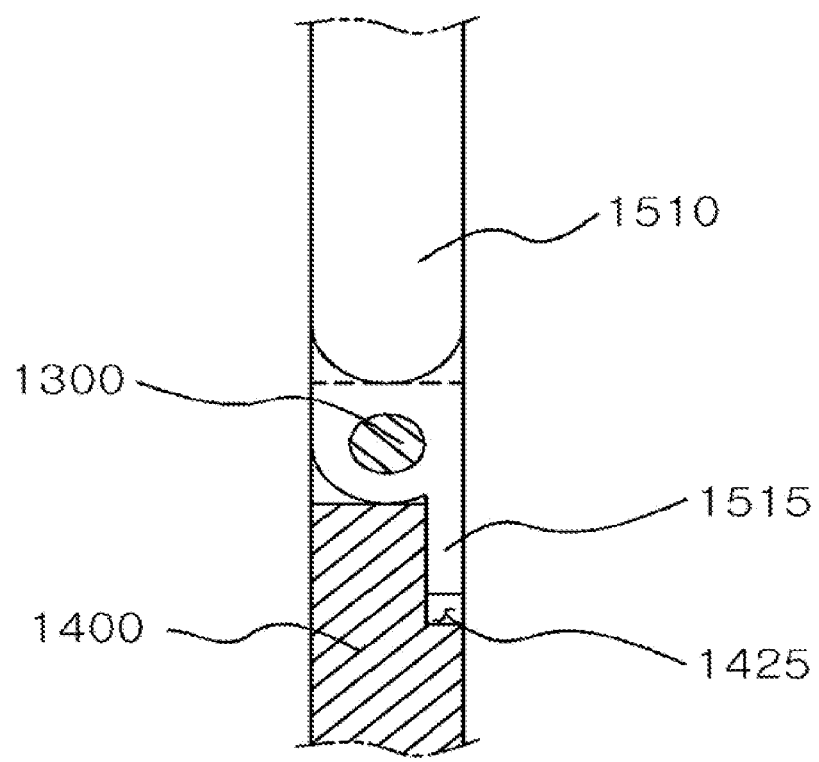

As a similar shape, a shape shown in FIG. 9 is also preferred.

FIG. 9 is a schematic partial enlarged view showing an exemplary application type of the deployment limiting means that may be further included in the spinal fixation device according to the embodiments of the present disclosure.

As shown in FIG. 9, the middle plate 1400 preferably has a limiter receiving groove 1425 in which the deployment limiter 1515 is seated.

As can be seen from FIG. 9, the middle plate 1400 has the limiter receiving groove 1425 in which the deployment limiter 1515 is seated, and when the deployment plate 1510 rotates 180° around the hinge coupling 1300, the deployment limiter 1515 is received in the limiter receiving groove 1425 and comes into contact with the middle plate 1400. Accordingly, the deployment limiter 1515 prevents the deployment plate 1510 from rotating any longer.

Figure 10:
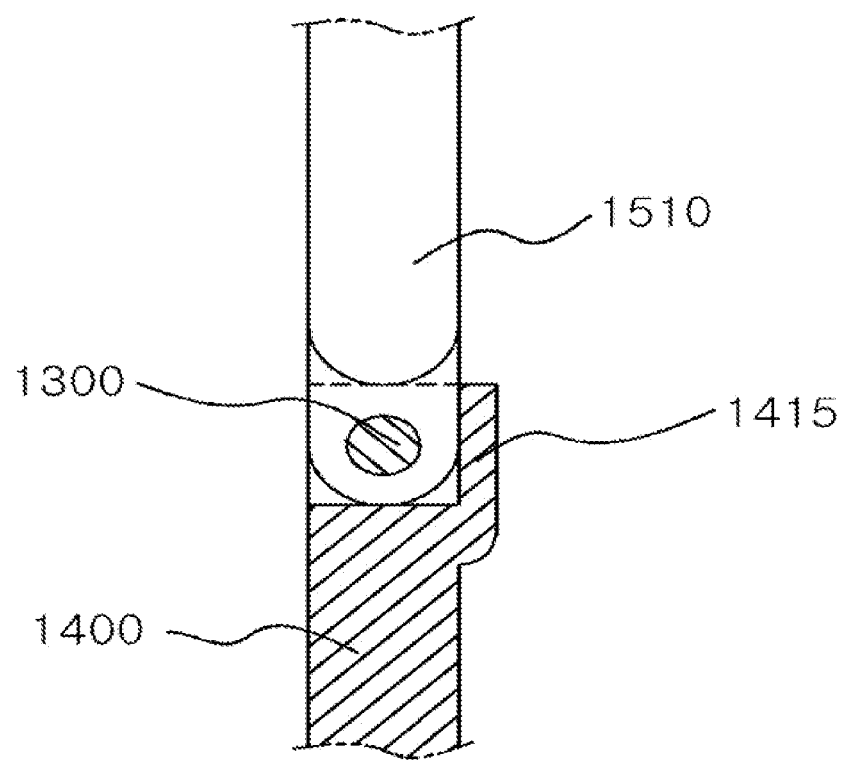

FIG. 10 is a schematic partial enlarged view showing another type of the deployment limiting means that may be further included in the spinal fixation device according to the embodiments of the present disclosure.

As shown in FIG. 10, a deployment limiter 1415 is provided on a side of the middle plate 1400, and it is possible to prevent the deployment plate 1510 from rotating any longer when the deployment plate 1510 rotating around the hinge coupling 1300 comes into contact with the deployment limiter 1415.

Figure 11:
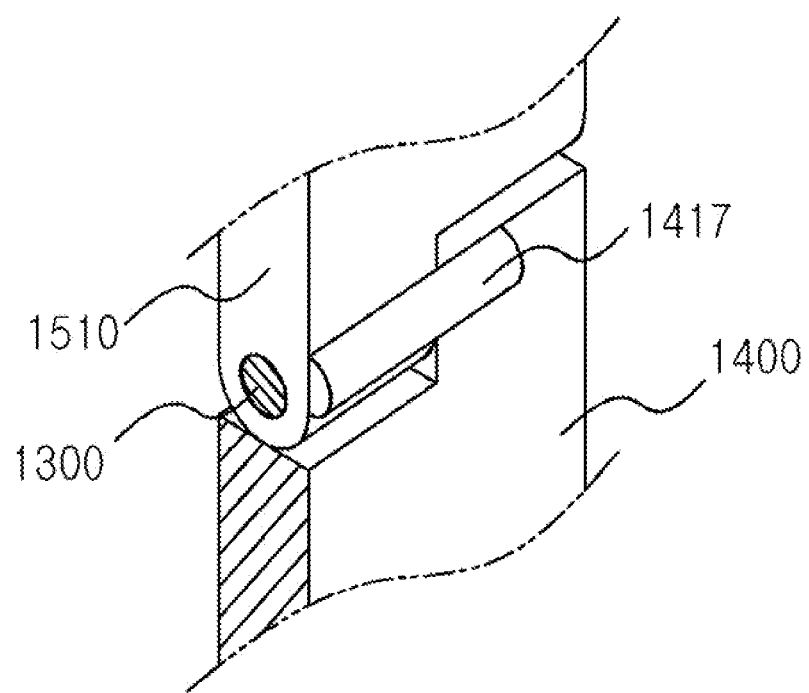

Meanwhile, a shape as can be seen in FIG. 11 is also possible.

FIG. 11 is a schematic partial enlarged view showing a modified type of the deployment limiting means that may be further included in the spinal fixation device according to the embodiments of the present disclosure.

As can be seen from FIG. 11, preferably, the deployment limiter 1417 is provided on the posterior side of the middle plate 1400, and comes into contact with part of the deployment plate 1510 to limit the further deployment of the deployment plate 1510 when the deployment plate 1510 is deployed by rotation to a predetermined angle around the hinge coupling 1300.

When the deployment limiter 1417 is formed in a part of the posterior side of the middle plate 1400 in a direction that is parallel to the axis of the hinge coupling 1300, the deployment plate 1510 comes into contact with the deployment limiter 1417 and cannot rotate any longer when the coupling angle of the deployment plate 1510 is 180°.

Additionally, the deployment limiter as described above with reference to FIGS. 8 to 11 may be provided in the spinal fixation device according to the second embodiment as described previously, and this is also preferred.

In the case of the spinal fixation device according to the second embodiment, the reference numeral 1400 in FIGS. 8 to 11 as described previously indicates part of the cage 110 (see FIG. 5), and for the other parts, the description made previously with reference to FIGS. 8 to 11 is equally applied.

The spinal fixation device according to the second embodiment or the first embodiment of the present disclosure as described hereinabove may be held and used in the cage holder as follows.

Figure 12:
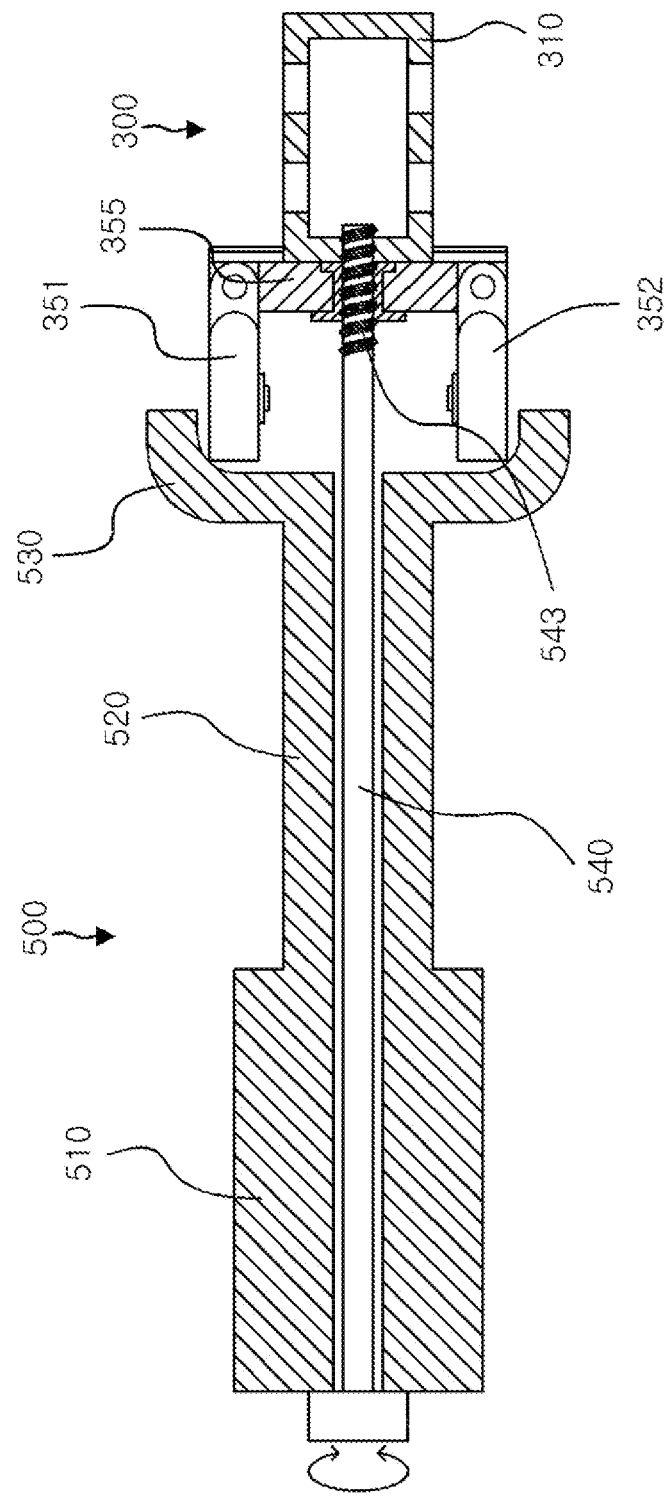
FIG. 12 is a schematic side cross-sectional view showing a spinal fixation device and a cage holder according to a first embodiment of the present disclosure.

FIG. 12 is a schematic side cross-sectional view showing the spinal fixation device and the cage holder according to the first embodiment of the present disclosure.

Referring to FIG. 12, the cage holder 500 holds the spinal fixation device 300. The cage holder 500 is an instrument provided for the user to manipulate and control to insert the spinal fixation device 300 between adjacent vertebrae.

The cage holder 500 includes a holder grip 510, a holder arm 520 and a holder rod 540.

The holder grip 510 is provided for the user to grip the cage holder 500, and is disposed on the posterior side of the cage holder 500. The holder grip 510 supports the holder arm 520 and the holder rod 540.

As shown in FIG. 12, the holder arm 520 has, at least in part, an internal space like a pipe, and the holder rod 540 is embedded in the space. The holder arm 520 protects and supports the holder rod 540 from the outside.

The holder rod 540 has a screw thread 543 at the anterior side end to hold the spinal fixation device 300. Additionally, when the anterior side end having the screw thread 543 in the holder rod 540 of the cage holder 500 is bolted to the holding hole of the middle plate 355, the spinal fixation device 300 may be held.

As the screw thread 543 is formed at the anterior side end of the holder rod 540, bolting coupling may be accomplished by insertion into the holding hole of the middle plate 355 of the spinal fixation device 300. By this bolting coupling, the spinal fixation device 300 is held in the cage holder 500.

Depending on the direction of rotation of the holder rod 540, coupling between the anterior side end of the holder rod 540 and the spinal fixation device 300 may be accomplished, or on the contrary, the coupling may be released.

Meanwhile, a support 530 is provided at the anterior side end of the holder arm 520. The support 530 holds in contact with part of the posterior side of the deployment plates 351, 352 hinge-coupled to the middle plate 355.

Figure 13:
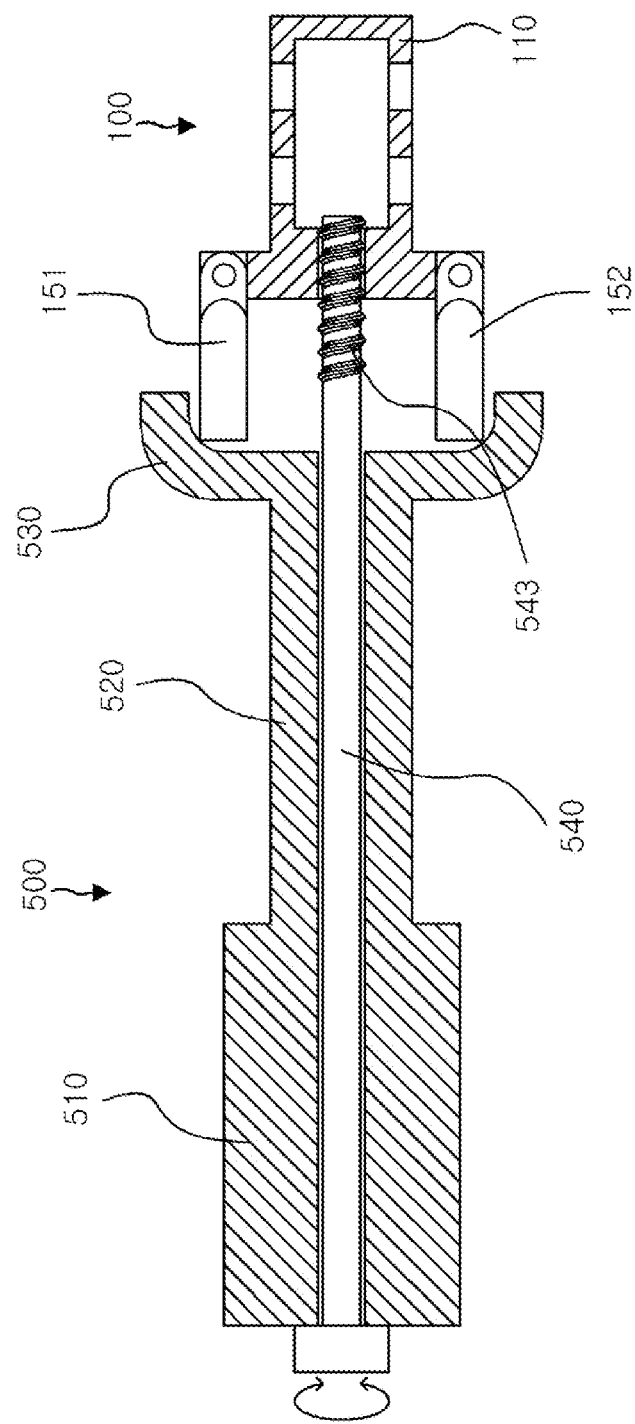
FIG. 13 is a schematic side cross-sectional view showing a spinal fixation device and a cage holder according to a second embodiment of the present disclosure.

FIG. 13 is a schematic side cross-sectional view showing the spinal fixation device and the cage holder according to the second embodiment of the present disclosure.

As shown in FIG. 13, the cage holder 500 holds the spinal fixation device 100. The cage holder 500 includes a holder grip 510, a holder arm 520 and a holder rod 540, and is similar to the previous description.

As mentioned previously in the spinal fixation device 100 according to the second embodiment, a holding groove or a holding hole, into which the anterior side end of the holder rod 540 may be bolted and inserted, is formed on the posterior side of the cage 110 of the spinal fixation device 100.

As a screw thread 543 is formed at the anterior side end of the holder rod 540, bolt coupling may be accomplished by insertion into the holding hole 196 provided in the cage 110 of the spinal fixation device 100. By this bolting coupling, the spinal fixation device 100 is held in the cage holder 500.

Depending on the direction of rotation of the holder rod 540, coupling between the anterior side end of the holder rod 540 and the spinal fixation device 100 may be accomplished, or on the contrary, the coupling may be released.

Meanwhile, a support 530 is provided at the anterior side end of the holder arm 520. The support 530 holds in contact with part of the posterior side of the deployment plates 151, 152 hinge-coupled to the posterior side of the cage 110.

The spinal fixation device according to the present disclosure as described hereinabove eliminates the need to place the plate after inserting the cage as conventionally, and can fix the cage between vertebrae accurately and stably, ensuring accuracy of cage insertion surgical procedure stably.

While the present disclosure has been hereinabove described in detail with regard to the embodiments with reference to the accompanying drawings, because the above-described embodiments have been described based on the preferred embodiments of the present disclosure, the present disclosure should not be understood as being limited to the above embodiments, and the scope of protection of the present disclosure should be understood from the appended claims and their equivalent concept.

| [Detailed Description of Main Elements] | |
| --- | --- |
| 110, 310: Cage | 130, 330: Hinge coupling |
| 151, 152, 351, 352: Deployment plate | 355: Middle plate |
| 170, 370: Bolt cover | 180: Fixing bolt |
| 190: Closer | |

What is claimed is:

1. A spinal fixation device, comprising:
a cage configured to be inserted between adjacent vertebrae and defining a gap;
a middle plate detachably coupled to the cage;
a plurality of deployment plates hinge coupled to the middle plate at one side end of each of the plurality of deployment plates, wherein the each of the plurality of deployment plates is rotatable to an arbitrary angle around the hinge coupling; and
a closer rotatably coupled on a posterior side of the middle plate, wherein when the closer is rotated, the closer prevents the plurality of deployment plates from folding.

2. The spinal fixation device of claim 1, wherein a holding hole is disposed at a center of rotation of the closer and is configured to accommodate a cage holder.

3. The spinal fixation device of claim 1, wherein the middle plate and the cage is selectively detachable by slide coupling.

4. The spinal fixation device of claim 1, wherein a height of the middle plate is greater than a height of the cage.

5. The spinal fixation device of claim 1, further comprising a deployment limiter disposed in the each of the plurality of deployment plates or the cage and limits a rotation of the plurality of deployment plates to a predetermined angle around the hinge coupling.

6. The spinal fixation device of claim 1, further comprising:
a fixing means to fix the plurality of deployment plates.

7. The spinal fixation device of claim 6, wherein the fixing means is a fixing bolt, and
the each of the plurality of deployment plates has a screw hole into which the fixing bolt is inserted.

8. The spinal fixation device of claim 7, wherein the each of the plurality of deployment plates has a bolt cover which covers at least a part of the screw hole and prevents a head of the fixing bolt from protruding out of the screw hole.

9. The spinal fixation device of claim 1, wherein an artificial bone space is disposed inside of the cage and accommodates an artificial bone.

10. The spinal fixation device of claim 9, wherein the cage has at least one artificial bone hole in communication with the artificial bone space.

11. A spinal fixation device, comprising:
a cage configured to be inserted between adjacent vertebrae and defining a gap;
a plurality of deployment plates hinge coupled to the cage at one side end of each of the plurality of deployment plates, wherein the each of the plurality of deployment plates is rotatable to an arbitrary angle around the hinge coupling; and
a closer rotatably coupled on a posterior side of the cage, wherein when the closer is rotated, the closer prevents the plurality of deployment plates from folding.

12. The spinal fixation device of claim 11, wherein a holding hole is disposed at a center of rotation of the closer and is configured to accommodate a cage holder.

13. The spinal fixation device of claim 11, wherein a step is disposed on a posterior side of the cage.

14. The spinal fixation device of claim 11, further comprising a deployment limiter disposed on a posterior side of the each of the plurality of deployment plates or the cage and limits a rotation of the plurality of deployment plates to a predetermined angle around the hinge coupling.

15. The spinal fixation device of claim 11, further comprising:
a fixing means to fix the plurality of deployment plates.

16. The spinal fixation device of claim 15, wherein the fixing means is a fixing bolt, and
the each of the plurality of deployment plates has a screw hole into which the fixing bolt is inserted.

17. The spinal fixation device of claim 16, wherein the each of the plurality of deployment plates has a bolt cover which covers at least a part of the screw hole and prevents a head of the fixing bolt from protruding out of the screw hole.

18. The spinal fixation device according to claim 11, wherein an artificial bone space is disposed inside of the cage and accommodates an artificial bone.

* * * * *